United States Patent [19]

Burritt

[11] Patent Number: 5,287,726
[45] Date of Patent: Feb. 22, 1994

[54] METHOD AND APPARATUS FOR LIQUID COOLED GENERATOR STATOR TEST AND PREPARATION THEREFOR

[76] Inventor: Hugh C. Burritt, Box 88; RR 110, No. Broadalbin, N.Y. 12025

[21] Appl. No.: 744,880

[22] Filed: Aug. 14, 1991

[51] Int. Cl.$^5$ .............................................. G01M 3/02
[52] U.S. Cl. .................................. 73/37; 73/40.5 R; 73/40; 134/21; 134/22.12
[58] Field of Search ................ 73/49.1, 49.5, 40.5 R, 73/37; 310/52, 59; 134/22.12, 22.11, 21

[56] References Cited

U.S. PATENT DOCUMENTS

| | | | |
|---|---|---|---|
| 3,877,293 | 4/1975 | McKeage | 73/49.1 |
| 4,417,465 | 11/1983 | Noe et al. | 73/40.5 R |
| 4,423,622 | 1/1984 | Bartlett | 73/49.5 |
| 4,697,665 | 10/1987 | Scharton et al. | 134/21 |

*Primary Examiner*—Hezron E. Williams
*Assistant Examiner*—Michael Brock
*Attorney, Agent, or Firm*—Schmeiser, Morelle & Watts

[57] ABSTRACT

Method and apparatus for preparing stators of a fluid cooled generator for ground (megger) and other tests. The method of automatically cycling into stator cooling coils gradually incremented pressures of super-desiccated air followed by subsequent rapid blowdown literally urges pockets of moisture out of the coils, freeing them by staccotic erosion or deterioration, as droplets and vapor. The process is carried out through the use of a palletized vacuum subsystem and conditioned air treatment/pressurization subsystem which includes a panel containing relay control logic for semi-automatic-/automatic conduct of the testing protocol and including essentially relay logic, an air compressor with necessary valving, air filtration and drying apparatus, a receiver which affords storage of the treated, dried air and a sequencing valve with adjunct equipment for connection of the receiver output to the stator-under-test. Also included is an off-pallet valve of the butterfly type which functions as the blowdown sequencing valve and is fixed to the outlet portion of the stator network which is undergoing purge/test.

9 Claims, 8 Drawing Sheets

LPC$_{(C/O)}$ = LOW PRESSURE CONTACT (CLOSED/OPEN)
HPC$_{(C/O)}$ = HIGH PRESSURE CONTACT (CLOSED/OPEN)

METHOD AND APPARATUS FOR LIQUID COOLED GENERATOR STATOR TEST AND PREPARATION THEREFOR

BACKGROUND OF THE INVENTION

I. Field of the Invention

This invention relates to the purging and non-destructive testing of dynamoelectric equipment typically utilizing a branched fluid cooling system, as well as to transformers. Specifically, the invention apparatus consists of an automatic and adjustable self contained unit which forces fluids and contaminants from without conductive cooling tube-equipped stators/transformers with cycles of compressed air, in periodic escalating pressures, holds the pressures in order to test integrity, and ultimately switches to high vacuum for final evacuation, test and preparation for subsequent conductivity (megger) testing. Integral, automatic and highly flexible, the invention finds its greatest application in rotating electrical equipment stator cooling systems.

II. Discussion of the Relevant Art

Large dynamoelectric equipment, such as generators, typically use branched fluid cooling systems. Parts of this equipment, such as the stator coils, are internally cooled by the circulation of a liquid such as water or oil. Generally, the operational atmosphere of these parts is pressurized hydrogen. The pressure of the coolant in the coil is less, by design, than the pressure of the hydrogen ambient pressure. Theoretically, a leak in a coil carrying coolant should allow the entry of hydrogen to the coil rather than venting of fluid to the atmosphere. Unfortunately, a bubble of such hydrogen gas within the coil is sufficient to at least partially block passage of the fluid coolant, thus creating hot spots which deteriorate stator insulation, diminish conductivity and ultimately cause shut-down of the equipment.

Periodic tests of conductivity of the stators are useful in prevention of accidents and unscheduled shut-downs of the equipment. The results of such tests depend, to some extent, on the degree to which all fluids and contaminants are first removed from the cooling lines. Periodic test protocols are also useful for determining advanced warning of breakdowns in the integrity of the lines, however minute. I have made this invention, specifically, to perform both services on the aforementioned dynamoelectric equipment.

SUMMARY OF THE INVENTION

Although speaking generally hereinafter of stator coils, stator cooling, conductor coolant or cooling lines, the reader should realize that such terms refer to the comparatively small lines which, although serving as electrical conductors, also transport coolant through the aforementioned dynamoelectric/transformer equipment and which are attached or manifolded to one another by pipe connectors. Depending on the style of connector, as well as the dynamoelectric equipment of the size (contemplated and) generally discussed hereinafter, there is an acceptable leakage of gas into the coolant through such connectors of approximately 3–5 cubic feet per 24 hours. This rate must be considered when interpreting the results of the pressure and vacuum degradation tests performed by the instant invention.

This invention evacuates all fluids, vapor and other contaminants from the interior of the stator conductors (cooling lines) of the generator to prepare it for subsequent and more accurate ground testing. In the course of this preparation, the invention also tests the integrity of the stator for the most minute leaks. Generally, the evacuation is accomplished through a series of escalating pressurizations performed on the stator cooling system using compressed air from a rotary screw compressor. It is then passed through a miniaturized twin tower desiccant air dryer and filter(s) in order to acquire a super-dry, completely contaminant-free (down to 0.01 micron) state.

According to the instant method, the preparation and test unit conducts a sudden and automatic blowdown of the cooling system that has been charged with dry, contaminant-free air to atmosphere, forcing the pressurized air contained in the stator to carry with it fluid and contaminants. The automatic blowdown will occur when a pre-determined high pressure setting, that has been established at the relay-logic central control and monitor panel, is satisfied. The evacuated or blown effluent passes through an automatic blowdown valve controlled from the aforesaid main control panel. Thus, the blowdown valve initially seals the stator coil at the discharge end until signaled by the main control panel to open. Eventually, a condition is reached when the discharge contains no visible fluids or solids. Progress toward this point is monitored by visual observation of the discharge itself and by reference to a panel-mounted analogue digital dewpoint gage.

Upon reaching the implied (only) vapor remaining stage, the remaining vapor molecular contaminants are removed from the stator by drawing a vacuum to as low as 5 microns. This is also held for adjustable time periods as a final degradation test of the stator's integrity. The above equipment, which I term salient to the invention, is mounted on a single skid and connected and controlled by the aforesaid central control and monitor panel, from which the pressure, vacuum and duration of cycles (and high and low pressure limits) are set, inlet and discharge dewpoints are observed and the success of each degradation test is monitored.

Turbine stator cooling coils must be periodically purged and tested. Previous practice, consisting of irregular blowdown (or purging) with ordinary compressed air (shop air) lead to two costly alternatives. Some power stations protracted the blowdown process, hoping that "overkill" would be the equivalent of success. This was an obvious extreme which cost valuable and unnecessary down time. Alternatively, others abbreviated the blowdown and completed the process with a vacuum purge. However, the liability of significant quantities of remaining water, particularly as a fluid, is not offset by the capability of vacuum to serve as an efficacious purging process. As I have proven, levels of vacuum low enough to be effective as a purge are also low enough to freeze (and concomitantly, internally fix) water.

In comparison with existing methods of preparing the stators of a fluid cooled generator for conductivity (megger), and later more destructive testing, this invention provides the operator with significantly greater advantages in speed, safety and efficiency. The current practice of blowdown with shop air provides no indication of the quantity of water remaining in the coils, no matter the duration of the process. Worse, this practice of steady application of fairly constant-level compressed air allows trapped pockets of moisture to be passed over as the air moves to discharge along the path of least resistance.

The instant invention's method automatically cycles, with a unique pressure incrementation/sudden blowdown feature that literally urges pockets of moisture, by a variable series of staccato "bumps", freeing them from local spots by erosion/deterioration as droplets and vapor. The process is controlled by relay logic which allows the buildup of highly desiccated air in a tank which is connected to the inlet port of a stator element and blocked at an outlet port thereof by a specially sequenced butterfly (blowdown) valve. Further, hygrometer probes attached to the blowdown or discharge valve allow the operator to accurately monitor the process of water evacuation by both visually checking the moisture effluent and, subsequently, by a constant comparative reading of the moisture content of the discharge air versus the inlet air which is displayed on suitable instrumentation located in the control panel containing the aforesaid relay logic.

In contrast to the current industrial practice of physically cycling the various inlet and discharge valves, my invention provides valuable protection against human error. Its auto-cycling feature removes the risk of a "skipped" cycle in the unlikely event that the operator should attempt to replicate this wave process with continual manual opening and closing of valves. It also protects against the attendant risk of shocking the stator by venting highly pressurized air into the cavity, caused by overlooking the need to pressurize the stator concurrently with the compressor's (receiver) tank. The invention affords an operator the assurance (rather than inference) of the accuracy of megger tests since the operator has more positive assurance that all water has been evacuated from the stator or that no more remains than the operator chose to leave. Although this is not a guarantee that subsequent testing of potentially destructive nature need not be required, it is, nonetheless, protection against the performance of unnecessary destructive tests which are based on inaccurate megger results.

The ability of the invention to detect leaks of minute size (through the pressure and vacuum degradation test modes), is enhanced by its further ability to pinpoint the location of these leaks with its optional helium infusion module and detector. This obviates the necessity o disassembling perfectly sound stators in a bundle-by-bundle search for the hole, costly in both the time it takes and in the risk of damage to the units. Thus, there is a set of equipment which I consider optional to the salient apparatus and this comprises a scrolling permanent test recorder, nitrogen purge tank and a plant air entry port. The recorder is mounted behind the master control panel (when used) and allows the operator to maintain, on paper, a permanent chronological record of the entry and discharge dewpoints of the air, duration and results of the degradation tests and time and pressure points of the blowdowns. The nitrogen purge tank is a mounted accessory which allows the operator the option of an additional drying and evacuation cycle between the pressurizations and the vacuum (or as an alternative to the vacuum in applications where the vacuum degradation test may be deemed unnecessary). Finally, a plant air entry port may be provided for installations where concern may lie with accelerating the initial stages of fluid water and contaminant purging. Actually, this comprises a quick disconnect and filter which allows plant compressed air (of unknown moisture content but filtered to 0.01 micron) to flow into the stator at the entry port as a supplement to the invention's filtered, super-desiccated air. Application of this option speeds the evacuation of fluid water and solids; but, should be discontinued as soon as the aforementioned point of only vapor remainder is approached.

DETAILED DISCLOSURE OF THE PREFERRED EMBODIMENT

In essence, my invention comprises a stator test module designed to purge all contents and dry the interior of a coolant coil, provide pressure and vacuum degradation tests of the coil's integrity and that of its seals and ensure the accuracy of subsequent conductivity tests. It is portable, within the meaning of the term as ascribed in the industry, and allows application of a methodology which may be either a function of routine maintenance or be regarded as a tool in the redress of system failure. The invention primarily addresses electric generation equipment which is cooled by a fluid running through the same narrow tubes (stators) which collect the charge from a rotor, but are not necessarily limited to such. The invention apparatus is quickly and easily connected to an inlet port of these stators by a sealed flange, disconnect and passage to a manifold which resides on the body of such (stator) equipment. Two stainless steel passages lead from the manifold to two manual ball valves (on both sides of each are pressure sensing probes serving the pressure side and vacuum sensing probes serving the vacuum side—both with digital read outs and functioning on the mimic buss of the flow diagram of the hereinafter disclosed central control panel), one ball valve (pressure) isolating a passage through an ASME coded steel receiver having an epoxy coated interior, through a solenoid valve, back pressure regulating valve, an air filter (to 1.0 micron), the first hygrometer probe, twin tower molecular sieve compressed air dryer (2 minus 100° F. approximate pressure due point) and then through a second and third filter (first to 0.01 micron, then to 1.0 micron), through an air cooled aftercooler and into the source of the compressed air, an electrically powered oil flooded rotary screw compressor mounted on the receiver's upper surface. The compressor's power supply line and control lines lead to the invention's central control panel. The tank includes both vacuum and pressure relief valves and is brought up to pressure concurrently with that pressure building in the stator under purge/test.

From the second manual ball valve at the manifold, a stainless steel passage leads past an electric solenoid vacuum relief valve (normally open, electrically closed) to a high efficiency electrically powered pump (complete with vacuum sensor and vacuum solenoid relief valve) capable of drawing vacuum as low as 1.0 micron. The pump also includes electrical sump heaters. The power supply line and control lines from the vacuum pump also lead to the invention's central control panel.

Leading from the control panel is an electric line to an electrically actuated stainless steel butterfly manifold attached to the stator's (or workpiece/assembly) discharge port. A one half inch rated vacuum manual ball valve is side-mounted to the stainless steel manifold assembly and is used for a downstream hygrometer probe and/or downstream vacuum or pressure readings. The butterfly valve has the capability of manual operation or autocycled operation on pressure demand, all controlled by the central panel controllers.

An operator, working from the control panel, may set the desired pressures to be applied to the stator (which, as aforesaid, is brought up to pressure simultaneously with the receiver in order to avoid undue stress or "shock" to the equipment), the high pressure point at which the discharge valve will suddenly release to atmosphere (blow down), the desired level of vacuum to be applied to the stator and the chronologic limits that either process may be run. Depending on the model of generator to which this invention is attached, the controls may be calibrated to accommodate inevitable (hence allowable) "pipe fitting" leakage.

From the control panel, the operator may (visually) monitor the dewpoint of compressed air entering the stator and the dewpoint of the discharge air. From these readings, and early visual observation of the discharge itself, the operator may determine the progress of water evacuation from the stator, down to and through the status of "vapor only". The operator may visually read the rate at which either pressure or vacuum decay over the (arbitrarily) set parameters of stator seal testing, here applying compensation for the allowable leakage.

Figure 5:
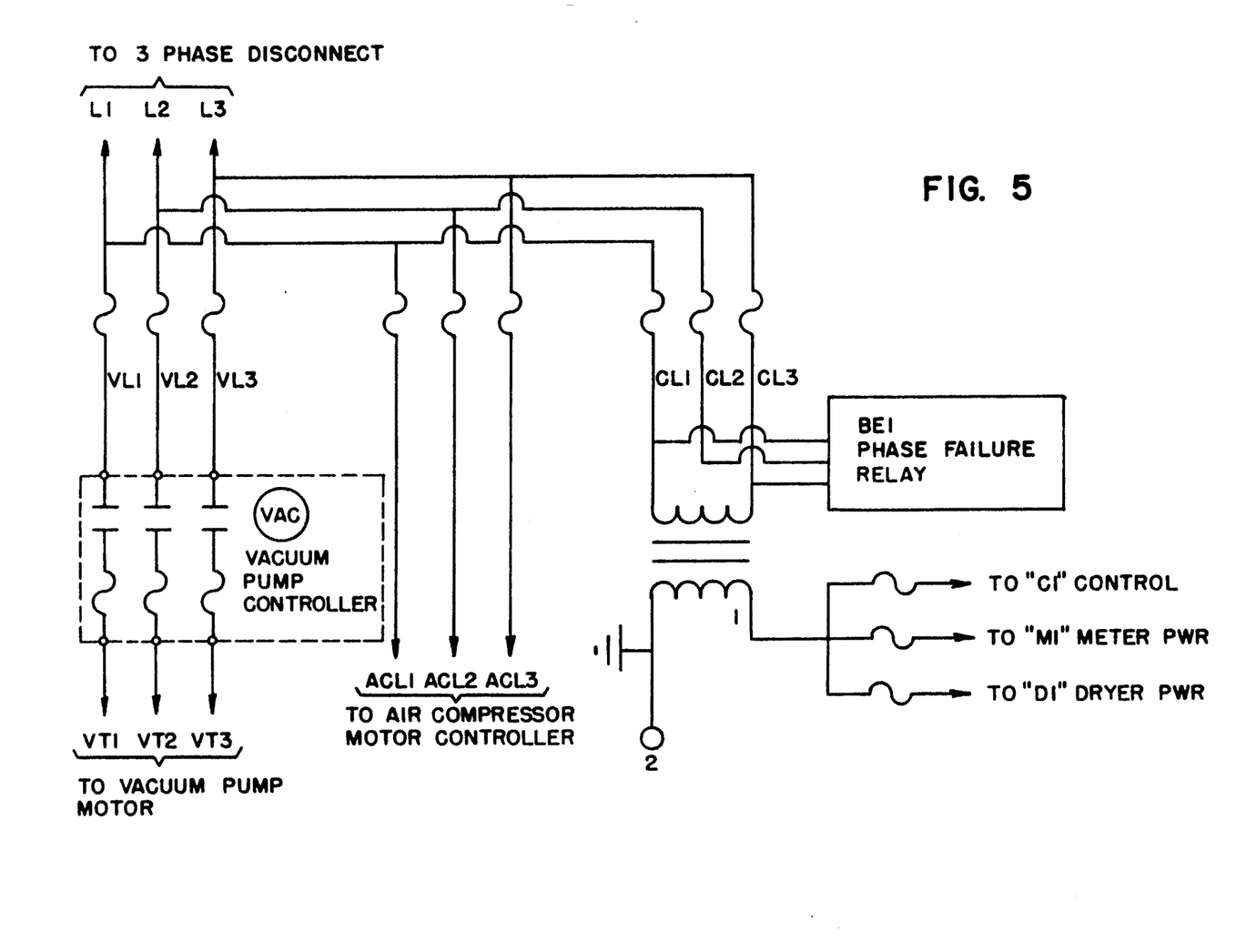
FIG. 5 is an electrical schematic of the main 480 volt 3 phase supply interface with the main circuits of the entire control system.

In order to discuss the electrical control which is exercised over the compressor, vacuum pump, filters, desiccators and valving which comprise the invention, I elect to use the schematic illustrations (FIGS. 5-11) in what I term a functional/electrical flow explanation. Referring more particularly to FIG. 5, there is disclosed an electrical schematic relating to the main 480 volt, three-phase (3Φ) power supply equipment that is used with the invention. It may be seen that 480 volts, (3Φ) power (L1, L2 & L3) are applied through a 3Φ fusible disconnect (not shown). Through the closed disconnect, power is applied through the vacuum pump fuses to points VL1, VL2 & VL3 at the line side of the vacuum pump motor starter. The air compressor is fused to points ACL1, ACL2 & ACL3 at the line side of the compressor motor starter. Power also flows through the closed disconnect to the control fuses at points CL1, CL2 & CL3, to the primary circuit of the control power transformer and 480 v. 3Φ power to the phase reversal relay BE1 (ensuring the proper phase sequence), distributing the power to all motors and the test module while protecting against the loss of proper phase conditions. Thus, the power input is fed to the control power transformer, which steps down 480 v. power to 120 v. control power at points 1 and 2. Point 1 applies power to the three control fuses: circuit C1 for control power; circuit M1 for meter power; and D1 for dryer power. Point 2 forms a grounded neutral common to the C1, M1 and D1 circuits. When energized, the vacuum pump controller VAC, applies 480 v. 3Φ power to vacuum pump motor points VT1, VT2 & VT3.

Figure 6:
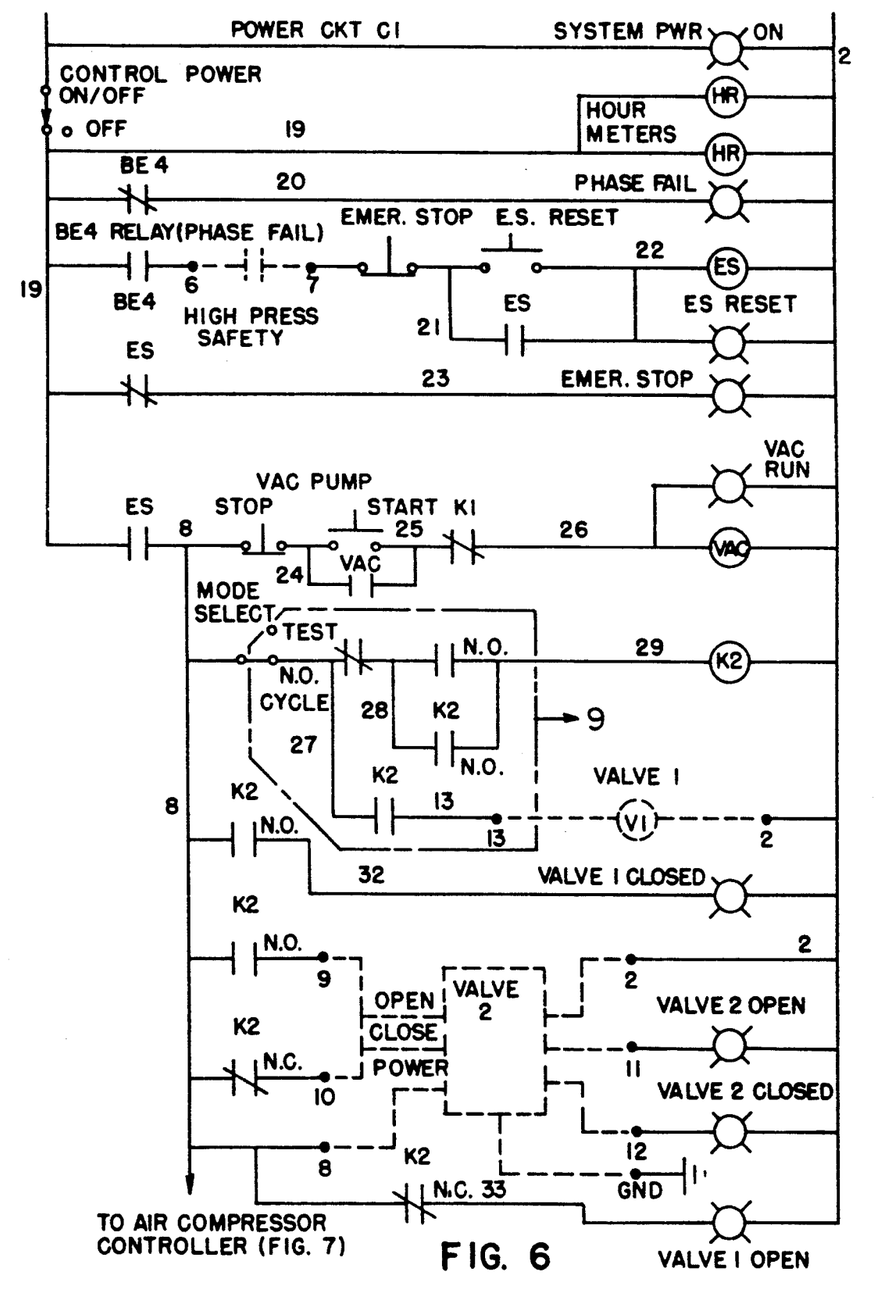
FIG. 6 is an electrical schematic of the system control.

Referring to FIG. 6 and beginning at the top of the page, 120 v. single phase (1Φ) AC power exists between control circuit C1 and point 2, causing the "SYSTEM POWER LIGHT" to be energized closing the control power switch applies power to point 19, which feeds the hour meters, two contacts on BE1 "PHASE FAILURE RELAY", and two contacts on ES "EMERGENCY STOP RELAYS"

When proper phase sequence is sensed by BE1 (FIG. 5), power flows to point 6. However, if the BE1 phase failure relay conditions are not met, power is denied at point 6 and applied at point 20, which causes the red phase failure light to be energized.

If power is present at point 6, it flows through the high safety switch to point 7, the "EMERGENCY STOP" push button. Power flows through the normally closed ES push button to the normally open ES reset push button and to a normally open ES relay contact (point 21). Depressing the ES reset button allows power to flow to point 22, causing both the ES relay and the green "EMERGENCY STOP" reset light to be energized. The relay is sealed by ES contact between points 21 and 22. If the high air pressure limit (generally 100 psig) is exceeded, or the "EMERGENCY STOP" button is depressed, or the BE4 relay trips, the ES relay will deny power to point 8 and apply it at point 23 causing the "EMERGENCY STOP" light, on the main control panel 22, to be energized.

If power is present at point 8, it is supplied to the normally closed "vacuum pump stop" push button. Power flows through the button to point 24, which applies the power to the normally open "START VACUUM PUMP" push button and a normally open auxiliary contact on the vacuum pump controller VAC. Depressing the start button applies power to point 25 which, in turn, applies power to the normally closed K1 relay The K1 contact between points 25 and 26 prevents the vacuum pump motor from being started if the air compressor is running. If power is applied to point 26, the vacuum pump controller will be energized and the "VACUUM RUN" light will be illuminated.

Figure 9:
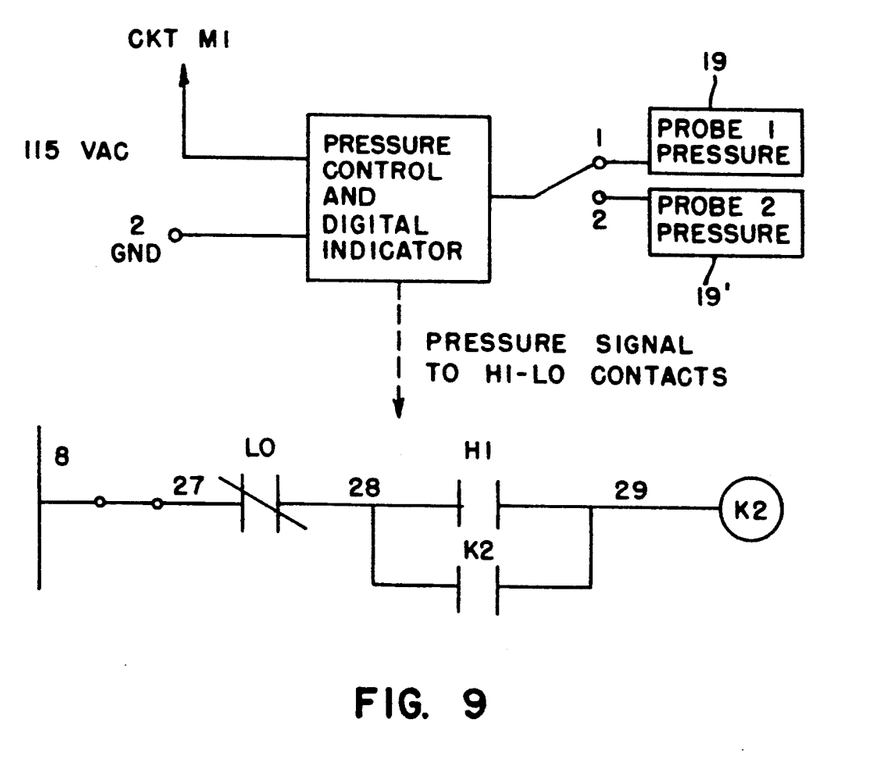
FIG. 9 is a combination functional diagram and detailed schematic of pressure control circuitry in the system control circuit of FIG. 6.

Should power be present at point 8, it is applied to the "MODE SELECTOR" switch. If this switch is in the "CYCLE" position, power is applied to point 27, which applies power to both the normally closed (N.C.) pressure controller contact (LO) and a normally open (N.O.) (HI) contact (see also FIG. 9 detail). Power then flows through the pressure controller contact to point 28, which feeds a second K2 contact on the pressure controller. When pressure builds to a preset level, the normally open controller contact closes applying power to point 29, causing the K2 relay to be energized. FIG. 9 details the circuitry at this point in FIG. 6, integrating it with the functional flow of pressure control and digital indicator and the probe 1 and 2 pressure sensors.

Resuming the discussion of FIG. 6, the K2 relay is latched (sealed) by the K2 contact between points 28 and 29. When the K2 relay causes contact closure, power is applied to points 9, 13 and 32. Thus energized, power at point 9 causes valve #2 to open. When fully opened, point 11 is energized and "VALVE #2

OPEN" light on the panel is energized. Power at point 13 energizes pneumatic valve #1, closing off air flow through the valve. When point 32 is energized, "VALVE #1 CLOSE" light is illuminated. System pressure will now decay to a pre-set level, at which point the normally closed pressure controller contact between points 27 and 28 opens, withholding power to the K2 relay, which in turn, denies power to points 9, 13 and 32, while applying power to points 10 and 33. Power is then applied through point 10 to the motor which closes valve #2. When valve #2 is fully closed, power is denied to point 11 and applied to point 12 energizing the "VALVE #2 CLOSE" light on the control panel. Lack of power at point 13 causes valve #1 to open, allowing the air flow therethrough. At this time, point 33 is energized and the "VALVE #1 OPEN" light is illuminated.

The above sequence is continued with the "MODE SELECTOR" switch in the "CYCLE" position. If this switch is in the "TEST" position, it is not possible to energize the K2 relay; valve #1 stays open and #2 stays closed, both states indicated by the appropriate light. "TEST" mode is used in the testing of the high pressure safety limit.

Figure 7:
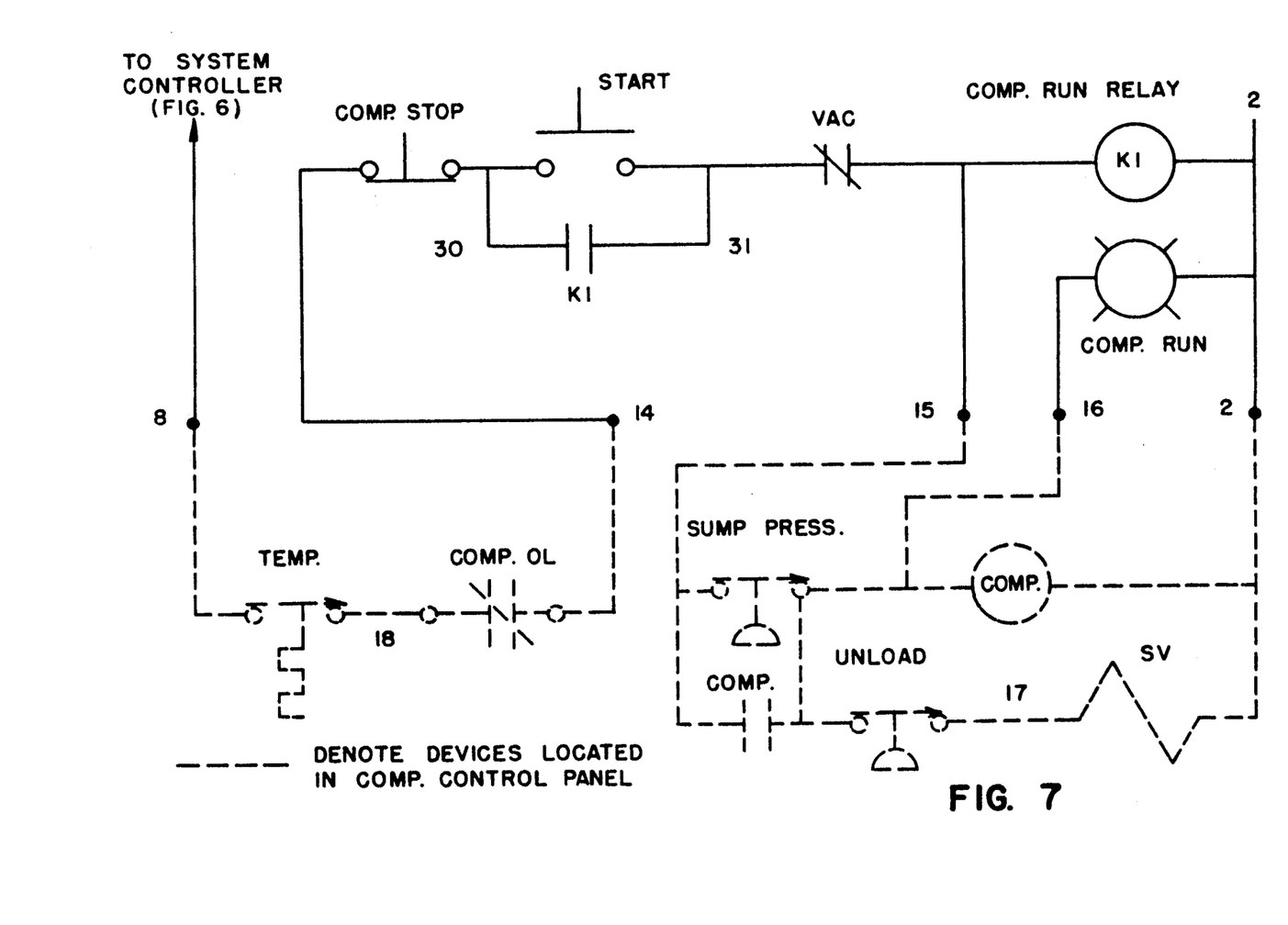
FIG. 7 is an electrical schematic of the compressor control.
Figure 8:
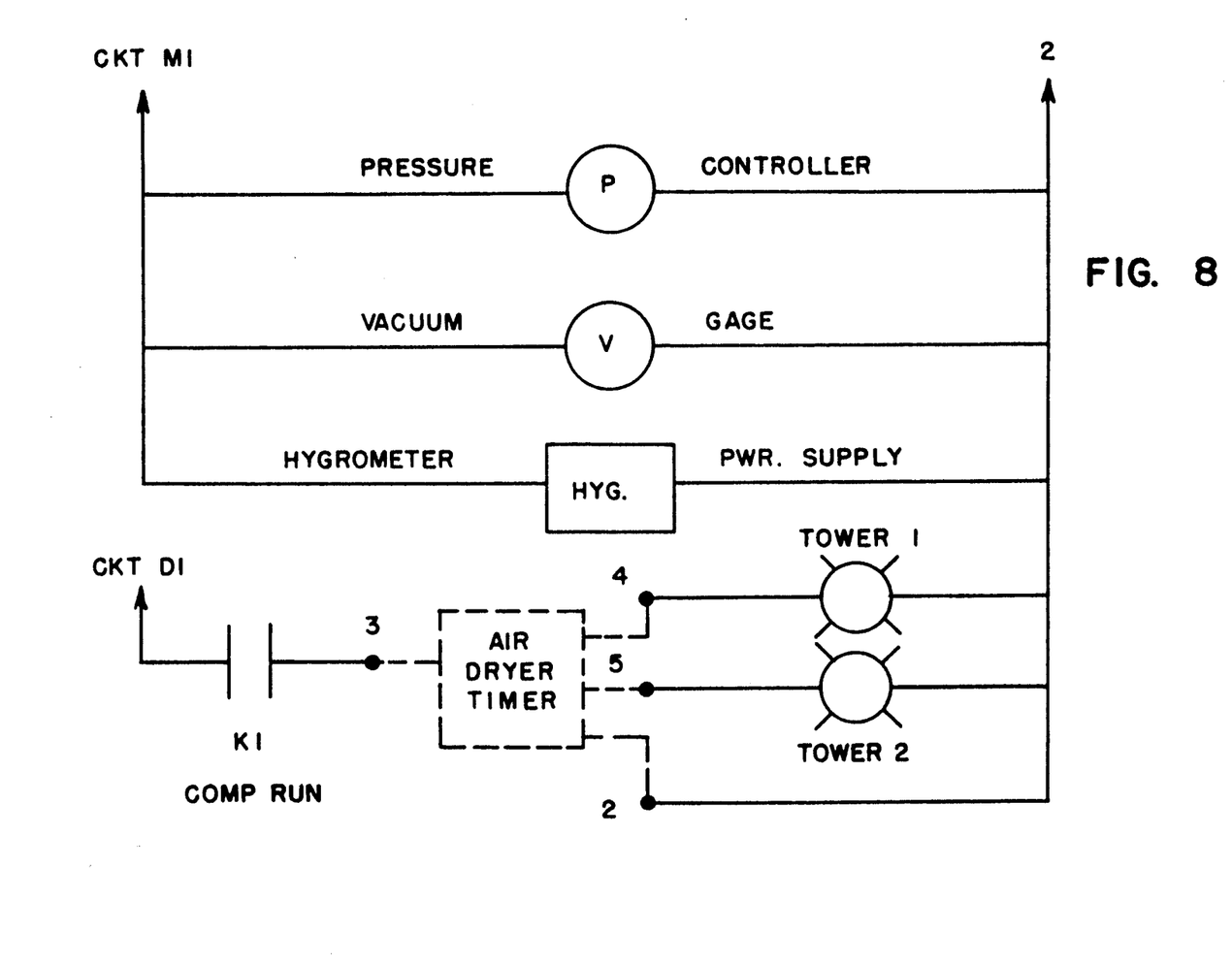
FIG. 8 is an electrical schematic of another portion of the control circuit.

The next point of interest in the control schematic concerns compressor 20 control which is now discussed with the aid of FIG. 7. The compressor starter receives power via point 8. Power flows through the high temperature limit switch to point 18, and then through the compressor overload to point 14 which feeds the normally closed "COMPRESSOR STOP" button. Power flows through the stop button to point 30, which feeds the normally open "COMPRESSOR START" button and the normally open K1 contact. Depressing the start button directs power to point 31 and hence to a normally closed vacuum pump auxiliary contact. This normally closed contact prevents start of the compressor when the vacuum pump is running (see previous discussion re: FIG. 6). When the vacuum contact is closed, power flows to point 15 and energizes the K1 relay. Point 15 directs power to the sump pressure switch and a normally closed compressor auxiliary contact. If the sump pressure is present, power is applied to point 16, energizing the compressor starter and illuminating the "COMPRESSOR RUN" light. The sump pressure switch is latched by the normally open compressor contact. When the compressor is energized (power to point 31), power is applied to the compressor unloader switch, which in turn energizes and deenergizes the compressor solenoid at point 17. High temperature, compressor overload, depressing the stop button or loss of power at point 8 will de-energize the controller, the point 15 and the K1 relay. Brief reference to FIG. 8 illustrates the conditions wherein circuit M1 applies 115 volt 1Φ AC power to the pressure controller, vacuum indicator and hygrometer power supply. Circuit D1 applies power to a normally open K1 contact, which remains closed while the compressor is running. This applies power to point 3, feeding power to the air dryer timer. The timer applies power to either tower #1 or #2 indicator lights, in sequence.

A most salient aspect of this invention is its application of compressed air in a specific cycle, that is, in an automatic pressure build-up and blowdown of the stator water cavities in circumstances when compressed air is used in the field testing of the stators. The instant process removes more water faster than manual continuous blowdown or a manual cycling of the blowdown involving manual opening and closing of valves. Further, the invention, through its unique apparatus and control gear, provides a clear gauge indication of the degree of water evacuation that is unavailable applying a purely manual process.

Figure 1:
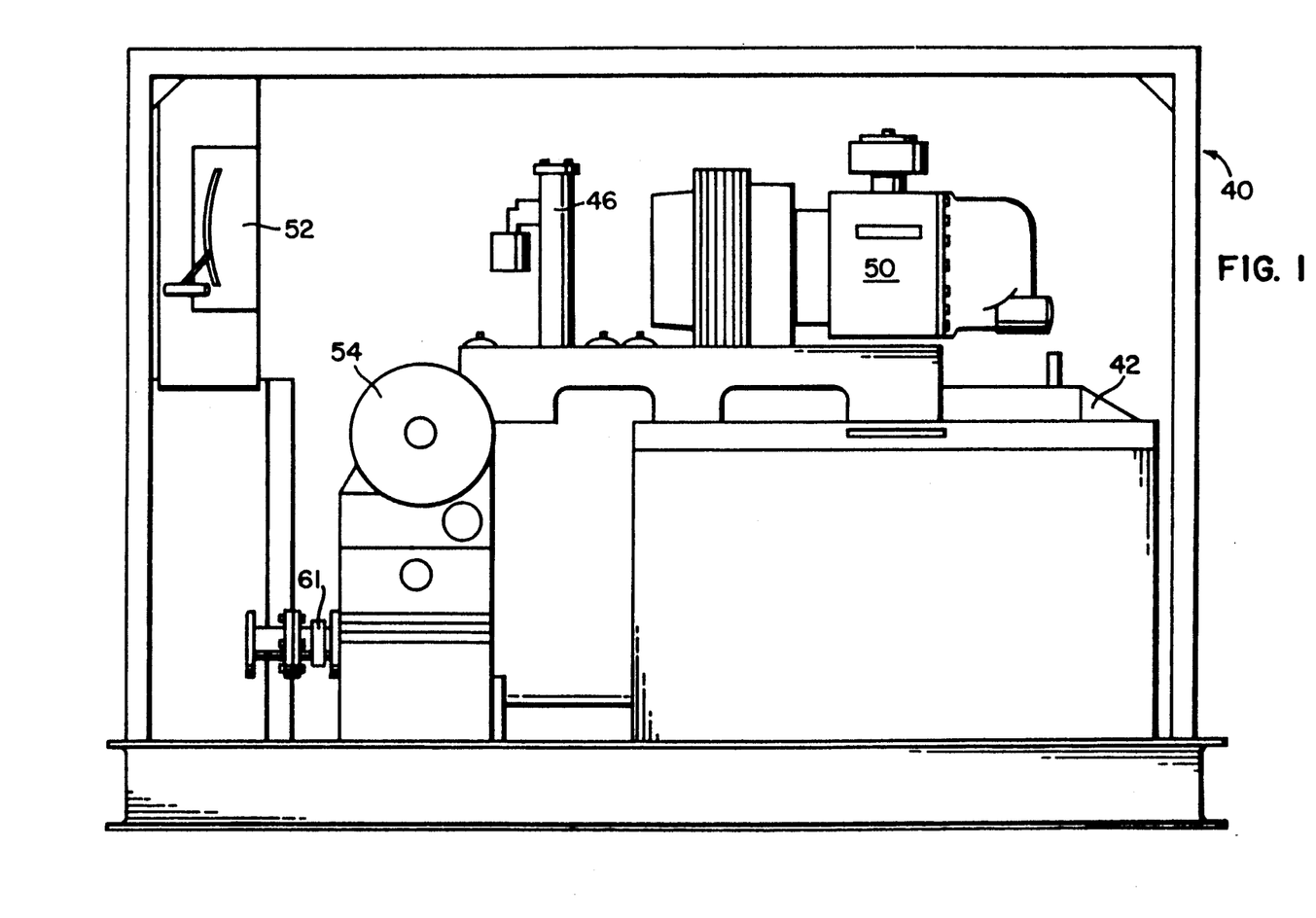
FIG. 1 is a (vacuum) side elevation of the invention.
Figure 2:
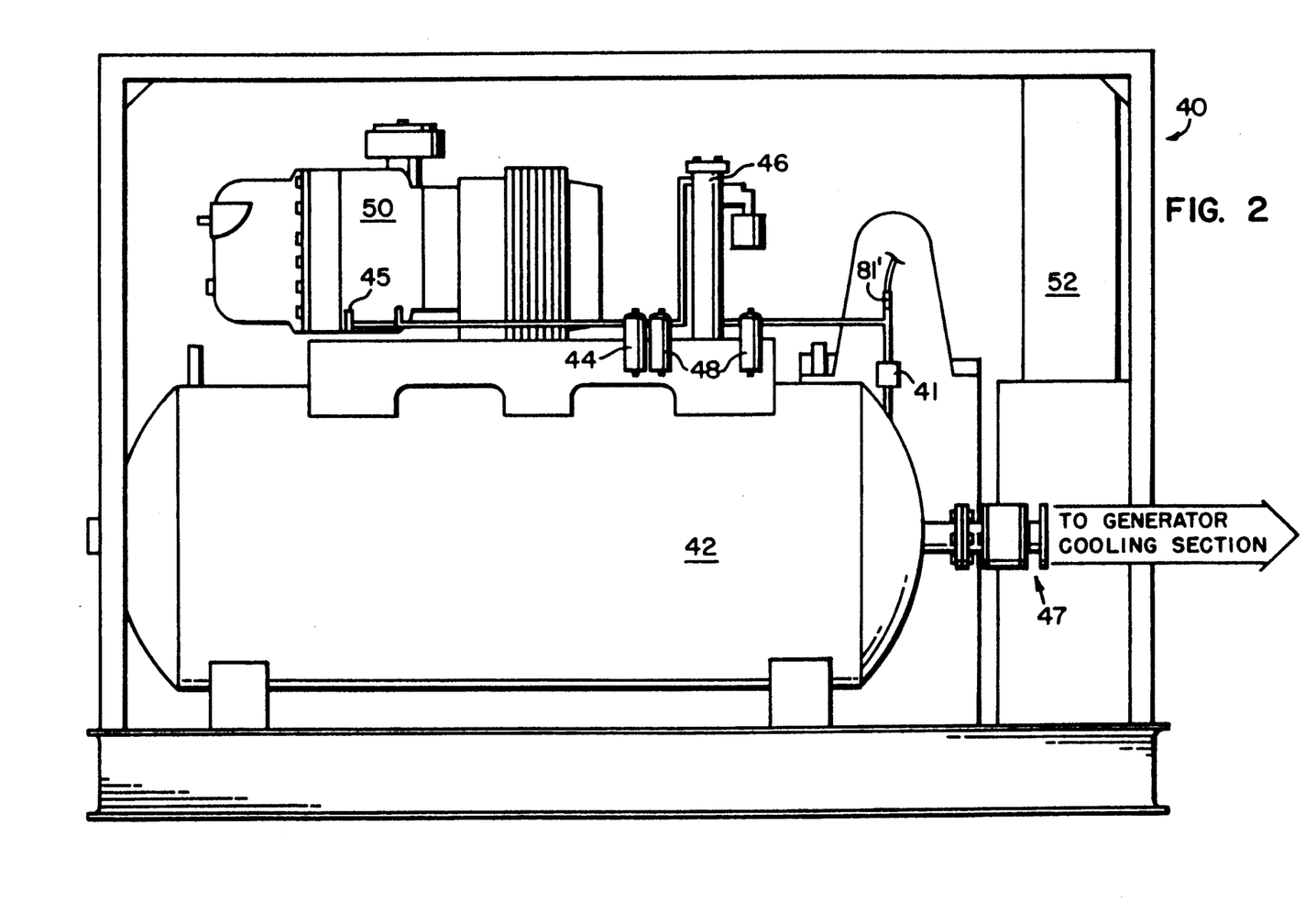
FIG. 2 is a (pressure) side elevation of the invention.
Figure 3:
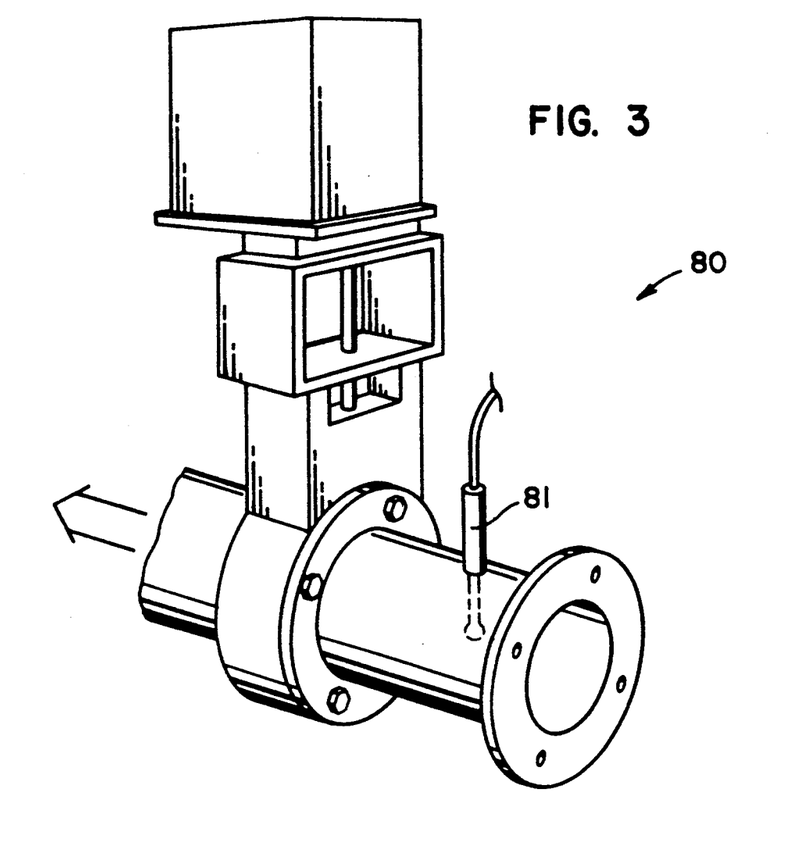
FIG. 3 is an isometric illustration of a butterfly (blowdown) valve and hygrometer probe assembly discharge manifold.
Figure 4:
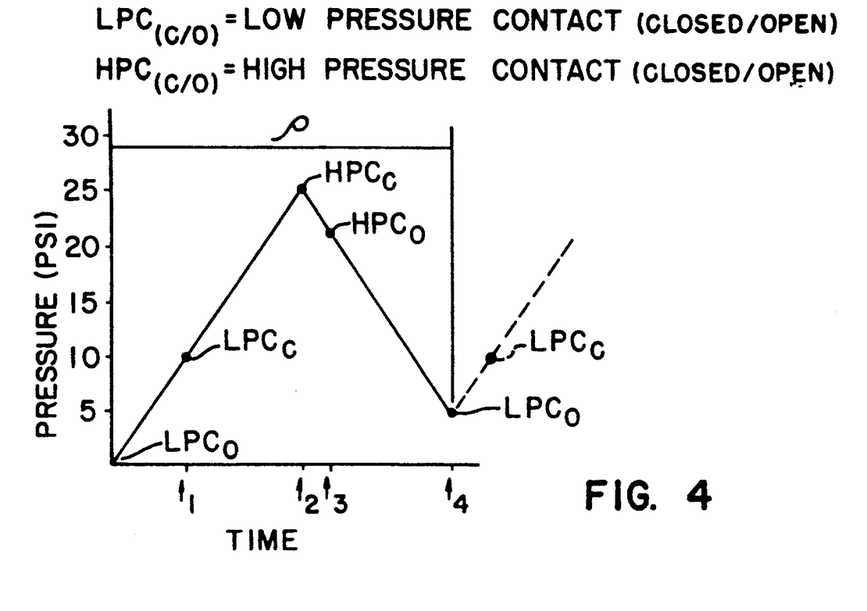
FIG. 4 is a pressure/time graphical presentation of low pressure contact and high pressure contact sequencing.

The automatic pressure cycling is achieved through the pressure controller and indicator in the control cabinet 52 through manipulation of both high and lower pressure adjustment knobs that are used to set the low and high pressure parameters of each cycle. Two pressure sensing probes 19, 19' (FIG. 9) transmit signals to the panel controller, which in turn opens and closes the pressure controller high and low contacts (see FIG. 6): low pressure contact (LO) between points 27 and 28 and high pressure contact (HI) between points 28 and 29. A typical (normal) cycling process proceeds as follows: the low pressure contact is set at $p_1$, say 10 psig and the high pressure contact is set at $p_2$, say 25 psig. The compressor is then started (FIG. 7 compressor start switch energized). Valve #2 (blowdown valve 80 of FIG. 3) is closed and valve #1 (inlet valve 41 of FIG. 2) is open. Compressed air builds in the stator cavity(ies) and the probes in the manifold (not shown) send back signals to the controller digital read out in the control panel. Although the contact between points 27 and 28 indicates "NORMALLY CLOSED", both pressure contacts are, in fact, open. FIG. 4 is a graphical illustration of this cycle.

Both contacts start in the open position; valve #1 is normally open, valve #2 is normally closed. As the compressor adds air to the closed system, the pressure is sensed by the manifold pressure probes 19, 19', and the low pressure contact between points 27 and 28 closes. Pressure continues to build until the high pressure set point is reached. At this pressure, the high pressure contact between points 28 and 29 closes. The K2 relay energizes, latching the K2 contact between points 8 and 9, points 8 and 32 and points 28 and 29. The K2 contact between points 13 and 27 closes valve #1, stopping the flow of air and consequently, the buildup of pressure. Contact K2 between points 8 and 9 opens valve #2, the blowdown valve 80. When the high pressure contact opens, it releases the air trapped in the stator assembly which bleeds to atmosphere until the manifold pressure probes sense that the set low pressure point has been reached, thus opening the lower pressure contact. Immediately the K2 relay is de-energized, causing the K2 contacts to open between points 13 and 27. Consequently valve #1 opens, allowing air flow into the stator cavity. The normally closed K2 contact between points 8 and 10 closes and valve #2 closes, allowing pressure to begin building anew in the stator. The cycle is then repeated based upon the periodicity selected by the operator. Located within the manifold (not shown) are probes which sense vacuum level and hygrometer probes (see FIG. 3, hygrometer probe 81 and FIG. 2 hygrometer probe 81') which sense moisture. Signals of these instruments are lead to digital and analogue read-out gauges only.

The rapid and automatic cycling of super-dry compressed air through the stator flushes it more quickly (and automatically) than may be done with conventional methods, while yet providing the operator with a previously unavailable knowledge of the extent of water evacuation from the stator.

My invention results in a considerable reduction in down time for the generator under test, with a bonus realized as a pre-test of the stator's integrity, through isolation of the system using valves 47 (pressure) and 61 (vacuum), recording the degradation of both the pressure and the vacuum (which can be permanently kept on a scrolling graph, as well as the recording of hygrometer readings). The advantage of capability to perform the vacuum and other adjunct tests is greatly enhanced by the presence of requisite equipment (such as nitrogen attachment at valve 45) which are on or attached to the pallet containing the salient invention elements. The use of such additional equipment is well within the scope of knowledge of testing personnel within the industry and shall not hereinafter be addressed. Use of this equipment and the method of this invention by those skilled in such cooling system purging and testing techniques will prove of inestimable value and may be practiced with fruitful results consistent with the hereinafter appended claims.

What is claimed is:

1. A portable, palletized system for purging coolant lines of transformers and/or dynomoelectric stators comprising:
   (A) a pallet,
   (B) pressurization and blowdown means for connection to coolant lines to be purged by systematic and automatic application of pressurization and blowdown operations,
   (C) and control means including a plurality of transducers operatively associated with the pressurization and blowdown means to regulate cyclical operation of the pressurization and blowdown means.

2. A portable, palletized system for purging fluid coolant lines of transformers and/or dynamoelectric stators comprising;
   (A) a pallet; said pallet bearing thereon at least
   (B) means for subjecting the fluid lines to a series of pressurization and blowdown operations, including,
       (i) a vacuum subsystem comprising a vacuum drawing means including a vacuum inlet valving means;
       (ii) an air compression subsystem comprising air compressor means, air conditioning means and compression inlet conduit means including compression valving means;
       (iii) a semi-automatic control means comprising essentially relay logic circuits for actuating said vacuum and compression valving means while responding to pre-set relays which are responsive to signals generated by a plurality of pressure transducers located proximate said vacuum and compression valving means, said logic circuits used to control the vacuum and the air compression subsystem and to conduct activation signals to both of said valving means, said logic circuits being further responsive to manual setting of pressure or vacuum thresholds so as to allow variations of pressure/vacuum parameters for pressure/vacuum operations performed by said system.

3. The system of claim 2 wherein said vacuum drawing means includes a vacuum pump.

4. The system of claim 2 wherein air compressor means includes a direct drive, rotary screw compressor for pressurizing air.

5. The system of claim 2 wherein air conditioning means comprises at least one twin tower heatless, regenerative air dryer for desiccating air.

6. The system of claim 5 wherein air conditioning means further comprises in-line prefilter means, coalescing filter means and afterfilter means for cleaning the desiccated air.

7. The system of claim 2 wherein the semi-automatic control means includes a mode-of-operation mimic buss, vacuum, pressure and moisture meters with pressure adjustment regulator and pressure switches, and at least one resettable hour meter.

8. The system of claim 2 further comprising a scrolling recorder for recording data which relate to purging operations and/or vacuum and pressure testing as performed using said system.

9. The system of claim 2 wherein said logic circuits further comprise at least one relay circuit adapted to respond to signals from off-pallet pressure probes by activating a first valve means for connecting and disconnecting an air reservoir to an off-pallet conduit network and a second valve means for exposing/isolating the network from ambient conditions, said at least one relay circuit further comprising manually adjustable contact settings for discriminating between at least one first threshold and at least one second threshold.

* * * * *